(12) United States Patent
Wehrle et al.

(10) Patent No.: US 9,585,700 B2
(45) Date of Patent: Mar. 7, 2017

(54) MEDICAL INSTRUMENTATION AND METHOD

(71) Applicant: Aesculap AG, Tuttlingen (DE)

(72) Inventors: Christian Wehrle, Volkertshausen (DE); Josef Kozak, Tuttlingen (DE); Jens Beger, Tuttlingen (DE)

(73) Assignee: Aesculap AG (DE)

( * ) Notice: Subject to any disclaimer, the term of this patent is extended or adjusted under 35 U.S.C. 154(b) by 25 days.

(21) Appl. No.: 14/630,726

(22) Filed: Feb. 25, 2015

(65) Prior Publication Data

US 2015/0305786 A1    Oct. 29, 2015

(30) Foreign Application Priority Data

Feb. 25, 2014 (DE) .................. 10 2014 102 398

(51) Int. Cl.
| | |
|---|---|
| *A61B 17/70* | (2006.01) |
| *A61B 17/88* | (2006.01) |
| *A61B 17/86* | (2006.01) |
| *A61B 17/17* | (2006.01) |
| *A61B 17/34* | (2006.01) |

(52) U.S. Cl.
CPC ...... *A61B 17/7074* (2013.01); *A61B 17/7083* (2013.01); *A61B 17/8605* (2013.01); *A61B 17/8863* (2013.01); *A61B 90/98* (2016.02); *A61B 17/1703* (2013.01); *A61B 17/7032* (2013.01); *A61B 2017/3413* (2013.01); *A61B 2034/2048* (2016.02); *A61B 2034/2055* (2016.02); *A61B 2090/067* (2016.02); *A61B 2090/0818* (2016.02); *A61B 2090/3983* (2016.02)

(58) Field of Classification Search
CPC .................. A61B 17/7074; A61B 17/7083
USPC ....................................... 606/86 A
See application file for complete search history.

(56) References Cited

U.S. PATENT DOCUMENTS

| | | | | |
|---|---|---|---|---|
| 5,622,170 A | * | 4/1997 | Schulz ................. | A61B 5/0064 356/141.1 |
| 7,749,232 B2 | * | 7/2010 | Salerni ............... | A61B 17/7083 600/424 |

(Continued)

FOREIGN PATENT DOCUMENTS

| | | |
|---|---|---|
| DE | 10 2010 016 448 A1 | 10/2011 |
| EP | 2 179 703 A1 | 4/2010 |
| WO | 2011020505 | 2/2011 |

OTHER PUBLICATIONS

German Search Report with partial translation issued in related German Application No. 10 2014 102 398.6, dated Oct. 30, 2014.

*Primary Examiner* — Ellen C Hammond
*Assistant Examiner* — Stuart S Bray
(74) *Attorney, Agent, or Firm* — RatnerPrestia

(57) ABSTRACT

Medical instrumentation includes two or, in particular, more anchoring elements for anchoring on body tissue, and a stabilization element via which the two or more anchoring elements are connectable. The instrumentation includes a sensor unit, a coupling unit for percutaneous selective coupling of the sensor unit to at least one anchoring element or to the stabilization element, and a data processing unit which determines from sensor signals of the sensor unit the position of the anchoring elements relative to one another and/or the position of at least one anchoring element relative to the stabilization element.

23 Claims, 9 Drawing Sheets

(56) References Cited

U.S. PATENT DOCUMENTS

| | | | | |
|---|---|---|---|---|
| 7,835,778 B2* | 11/2010 | Foley | ............... | A61B 34/20 600/407 |
| 8,734,432 B2 | 5/2014 | Tuma et al. | | |
| 2005/0119593 A1* | 6/2005 | Gallard | ............... | A61B 17/7074 600/594 |
| 2007/0213714 A1* | 9/2007 | Justis | ............... | A61B 17/7002 606/86 A |
| 2008/0051787 A1* | 2/2008 | Remington | ......... | A61B 17/7005 606/279 |
| 2008/0195102 A1* | 8/2008 | Glazer | ............... | A61B 17/7074 606/80 |
| 2010/0069919 A1* | 3/2010 | Carls | ............... | A61B 17/7083 606/130 |
| 2010/0100081 A1* | 4/2010 | Tuma | ............... | A61B 34/20 606/1 |
| 2011/0040340 A1* | 2/2011 | Miller | ............... | A61B 17/8863 606/86 A |
| 2011/0125196 A1 | 5/2011 | Quevedo | | |
| 2011/0196433 A1* | 8/2011 | Kleiner | ............... | A61F 2/442 606/86 R |
| 2011/0270262 A1 | 11/2011 | Justis | | |
| 2011/0295159 A1* | 12/2011 | Shachar | ............... | A61B 5/1114 600/594 |
| 2013/0066387 A1* | 3/2013 | Beger | ............... | A61B 17/7083 606/86 R |
| 2013/0072982 A1* | 3/2013 | Simonson | ......... | A61B 17/7083 606/267 |
| 2013/0197644 A1* | 8/2013 | Cloutier | ............ | A61B 17/7074 623/17.16 |
| 2013/0218142 A1 | 8/2013 | Tuma et al. | | |
| 2013/0245704 A1* | 9/2013 | Koltz | ............... | A61B 17/00 606/86 A |
| 2013/0268007 A1* | 10/2013 | Rezach | ............... | A61B 90/06 606/279 |
| 2014/0107659 A1* | 4/2014 | Walters | ............ | A61B 17/7074 606/102 |
| 2014/0225999 A1 | 8/2014 | Bracke | | |
| 2014/0277198 A1* | 9/2014 | Stad | ............... | A61B 17/7074 606/86 A |
| 2015/0032164 A1* | 1/2015 | Crawford | ............ | A61B 19/2203 606/279 |
| 2015/0100091 A1* | 4/2015 | Tohmeh | ............ | A61B 17/7083 606/279 |
| 2015/0201974 A1* | 7/2015 | DeRidder | ......... | A61B 17/7074 606/102 |
| 2015/0265320 A1* | 9/2015 | Hynes | ............... | A61B 17/7074 606/279 |
| 2015/0305786 A1* | 10/2015 | Wehrle | ............... | A61B 90/98 606/86 A |

* cited by examiner

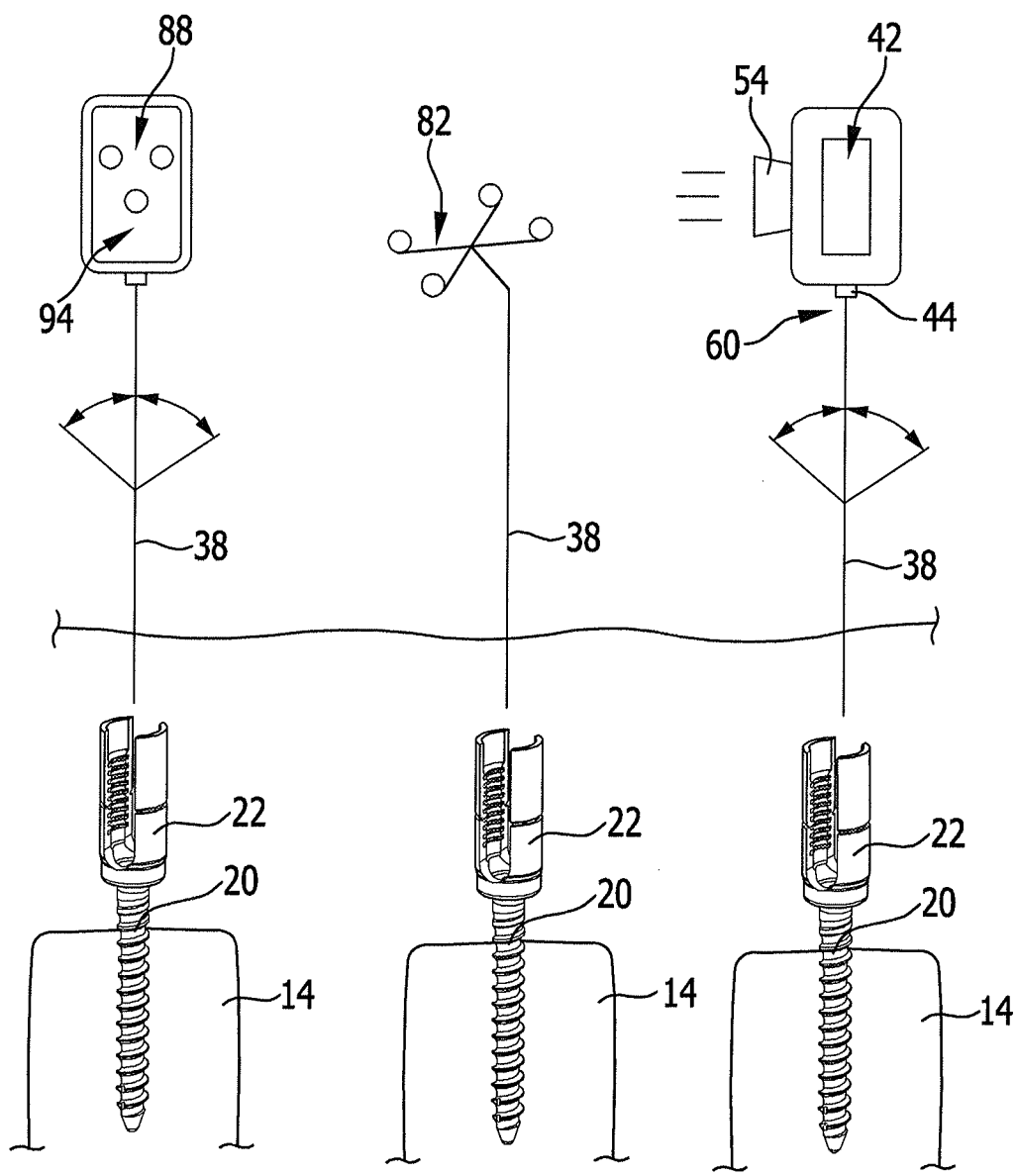

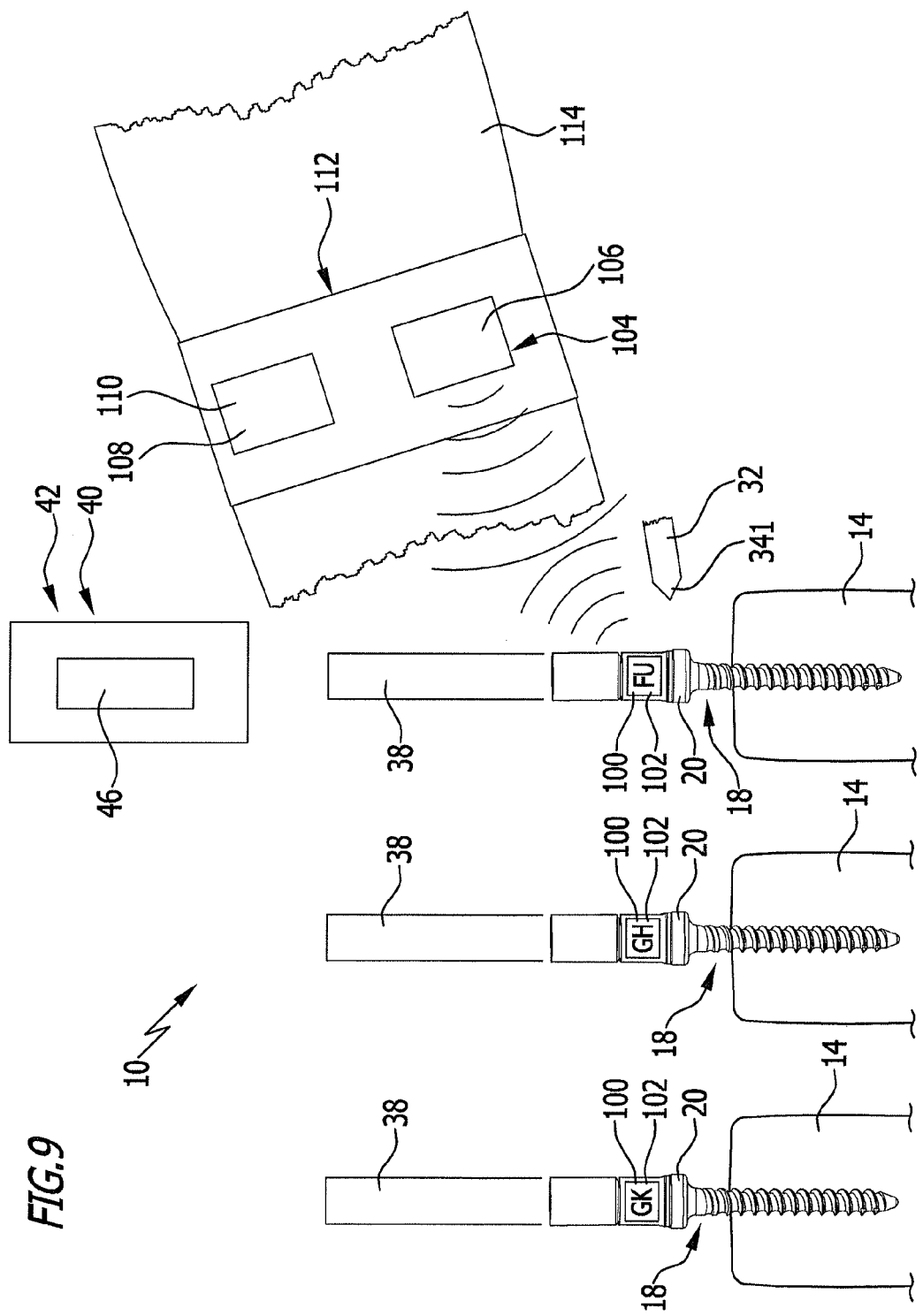

MEDICAL INSTRUMENTATION AND METHOD

RELATED APPLICATIONS

This application claims the benefit of priority of German Application No. 10 2014 102 398.6, filed Feb. 25, 2014, the contents of which is incorporated by reference herein in its entirety.

FIELD OF THE INVENTION

The present invention relates to a medical instrumentation, comprising two or, in particular, more anchoring elements for anchoring on body tissue and a stabilization element via which the two or more anchoring elements are connectable.

The present invention also relates to a method for using a medical instrumentation.

BACKGROUND OF THE INVENTION

A medical instrumentation of the kind mentioned at the outset is used, for example, in the treatment of vertebral fractures wherein anchoring elements in the form of bone screws are fixed to vertebral bodies and connected to one another via a stabilization element in the form of a rod. Here it is known to open the body tissue above the vertebral bodies and position the bone screws in the vertebral bodies under visual control. In a corresponding manner, the rod can be fixed under visual control to the bone screws which, for this purpose, may comprise, in particular, stabilization element receptacles into which the rod is to be inserted in a defined direction of insertion. To reduce the invasiveness, DE 10 2010 016 448 A1 proposes that the bone screws and/or the rod be localized percutaneously using an ultrasonic probe. The surgeon can thread the rod successively into the stabilization element receptacles of the bone screws under ultrasonic visual control.

In US 2013/0268007 A1 a method is described for percutaneously selectively measuring different sections of the rod attached to the bone screws with a probe. Herein the respective angle of the rod is determined in relation to a reference plane in order to determine the curvature of the rod. The curvature of the inserted rod is compared with a predetermined curvature to ensure that the vertebral column is stabilized in a desired position. This serves to treat and correct defective positions of the vertebral column.

A navigation system which can run on a handheld computer is described in EP 2 179 703 B1. The computer can be connected to a surgical instrument. Furthermore, a marking device is attached to the instrument, and its movement in space can be followed by a navigation camera arranged externally in relation to the computer. The data relating thereto are transmitted to the computer and processed by it.

An object of the present invention is to provide a medical instrumentation and a method for its use, which is more patient-friendly.

SUMMARY OF THE INVENTION

In a first aspect of the invention, a medical instrumentation is provided, comprising two or, in particular, more anchoring elements for anchoring on body tissue and a stabilization element via which the two or more anchoring elements are connectable. The instrumentation comprises a sensor unit, a coupling unit for percutaneous selective coupling of the sensor unit to at least one anchoring element or to the stabilization element, and a data processing unit which determines from sensor signals of the sensor unit the position of the anchoring elements relative to one another and/or the position of at least one anchoring element relative to the stabilization element.

In a second aspect of the invention, one of the aforementioned instrumentations, which comprises two or, in particular, more anchoring elements for anchoring on body tissue and a stabilization element via which the two or more anchoring elements are connectable, is used in a method. The sensor unit is percutaneously selectively coupled to at least one anchoring element or to the stabilization element via the coupling unit, and the position of the anchoring elements relative to one another and/or the position of at least one anchoring element relative to the stabilization element is determined by a data processing unit from sensor signals of the sensor unit.

BRIEF DESCRIPTION OF THE DRAWING FIGURES

The following description of preferred embodiments of the invention serves to explain the invention in more detail in conjunction with the drawings.

FIG. 8 shows schematically the use of the instrumentation from FIG. 1 for determining positions of the anchoring elements; and FIG. 9 shows schematically anchoring elements of the instrumentation with identification elements and a detection unit for successively detecting the identification elements.

DETAILED DESCRIPTION OF PREFERRED EMBODIMENTS OF THE INVENTION

Figure 1:
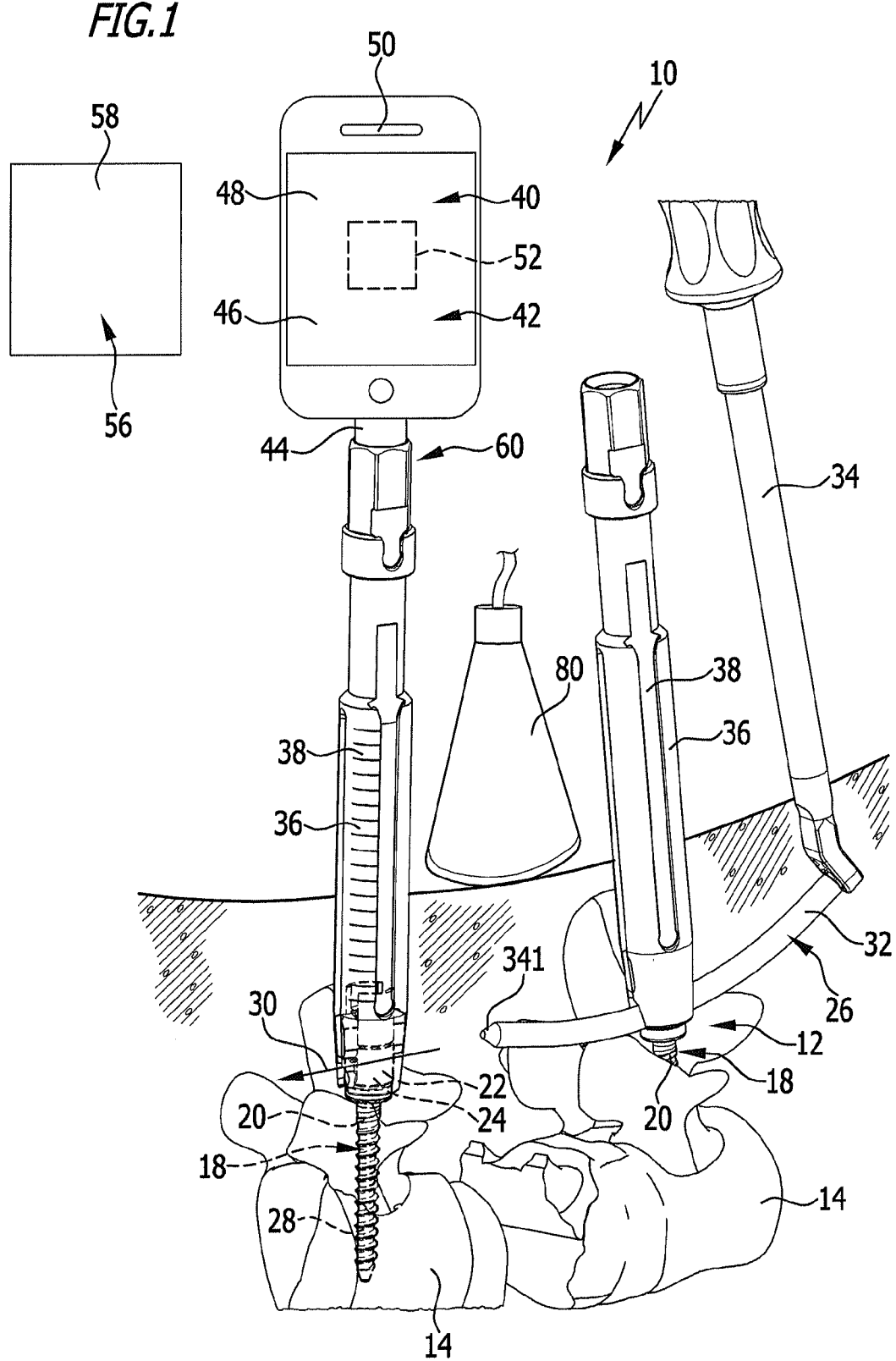
FIG. 1 shows a schematic representation of an instrumentation in accordance with the invention, with which a method in accordance with the invention can be carried out.

Although the invention is described and illustrated herein with reference to specific embodiments, it is not intended to be limited to the details described and shown.

The invention relates to a medical instrumentation, comprising two or, in particular, more anchoring elements for anchoring on body tissue and a stabilization element via which the two or more anchoring elements are connectable. The instrumentation comprises a sensor unit, a coupling unit for percutaneous selective coupling of the sensor unit to at least one anchoring element or to the stabilization element, and a data processing unit which determines from sensor signals of the sensor unit the position of the anchoring elements relative to one another and/or the position of at least one anchoring element relative to the stabilization element.

In the instrumentation in accordance with the invention, a sensor unit is used, which can be coupled via the coupling unit to at least one anchoring element or to the stabilization element. This allows the sensor unit to be brought into a defined relative position in relation to one or more anchoring elements or to the stabilization element. It is advantageous for the sensor unit to be able to be releasably coupled to the anchoring element or elements or to the stabilization element via the coupling unit. The data processing unit can determine from the sensor signals the position of the anchoring elements or of the stabilization element in a reference coordinate system of the sensor unit. It is also possible to determine the direction from one anchoring element to a further anchoring element. It is, therefore, possible, by percutaneous detection of subcutaneously located anchoring elements, to define a polygonal chain in the reference coordinate system. The position of the subcutaneously located stabilization element can also be defined in the reference coordinate system. The data processing unit can use the position and orientation of the polygonal chain, in particular, when the stabilization element is percutaneously inserted into the patient's body via an insertion tool, in order to connect the anchoring elements to one another. This is of advantage, in particular, when the position and/or orientation of the insertion tool and the stabilization element arranged thereon can be followed in the reference coordinate system via the data processing unit. This results in a particularly patient-friendly possibility of connecting the anchoring elements to one another via the stabilization element, with only small and minimally invasive incisions having to be made.

It may, in particular, be provided that the sensor unit can be successively coupled to at least one anchoring element via the coupling unit. Gradually, the positions of the anchoring elements and/or the directions of two anchoring elements following each other can be determined in the reference coordinate system. For example, the position of the stabilization element relative to the anchoring elements or vice versa can then be determined in order to connect these to one another. To determine the direction from a first to a second anchoring element, it is, for example, advantageous for the sensor unit to be connected via the coupling unit to both anchoring elements. This will be explained in more detail hereinbelow.

It is advantageous for the two or more anchoring elements to comprise a respective stabilization element receptacle into which the stabilization element is insertable in a direction of insertion, and for the data processing unit to determine from the sensor signals of the sensor unit the relative position of the stabilization element receptacles and the orientation of the respective stabilization element receptacle, with the coupling unit being positionable in a defined position and orientation in a reproducible manner at the stabilization element receptacle. This allows not only the position of a respective anchoring element to be determined but also the position and, in particular, the orientation of the respective stabilization element receptacle. This is advantageous for ensuring that the stabilization element receptacle is, firstly, correctly positioned and, secondly, oriented such that the stabilization element can be inserted into the stabilization element receptacle in a defined direction of insertion.

It proves advantageous for the sensor unit and an indication unit of the instrumentation to be integrated in the data processing unit and for this to be portable, in particular, in the form of a smartphone, handheld computer or tablet computer. In particular, this can be understood as meaning that an integrated unit is provided, which integrates the sensor system, the indication unit and the data processing. In this case, "integrated" can be understood, in particular, as meaning that the sensor unit and the display unit are arranged in a common housing, which also comprises the data processing unit. Handling of the integrated unit is user-friendly for the surgeon. By connecting the integrated unit to at least one anchoring element via the coupling unit, the integrated unit can be in the surgeon's field of vision at any time, which considerably simplifies the workflow.

The indication unit may be an optical display unit, in particular, with an image display, and/or an acoustic indication unit comprising, for example, a loudspeaker.

It proves advantageous for the sensor unit to comprise at least of the following sensors:
 a position sensor, for example, a GPS sensor;
 an inclination sensor with which an inclination and/or a change in the inclination of the sensor unit can determined;
 a compass sensor, for example, in the form of a magnetic field sensor, in particular, for determining the orientation of the sensor unit relative to the earth's magnetic field;
 an inertial sensor, in particular, for determining accelerations and/or rotation rates of the sensor unit;
 an optical sensor, in particular, a digital camera. The digital camera can, for example, detect a marking device which is connected to an anchoring element or to an insertion tool for the stabilization element, whereby these can be followed in space. The digital camera can also be coupled to an endoscope with which the position of the anchoring element, in particular, of a stabilization element receptacle of the anchoring element, can be subcutaneously detected.

The anchoring elements are, for example, bone screws, in particular, polyaxial screws with a respective stabilization element receptacle alignable in different orientations.

The stabilization element is, for example, a rod which is insertable, in particular, in a defined direction of insertion into a stabilization element receptacle of an anchoring element.

The coupling unit comprises, for example, an access tube or forms such an access tube, which is releasably connectable to an anchoring element in the form of a bone screw, in particular, is positionable in a defined position and orientation in a reproducible manner at a stabilization element receptacle of the bone screw. The anchoring element can be acted upon percutaneously through the access tube, for example, for clamped fixing of a rod on the bone screw.

Alternatively or additionally, the coupling unit can comprise or form an insertion tool for the stabilization element, which is releasably connectable to the stabilization element. In particular, the stabilization element can be attached in a defined position and orientation to the insertion tool. The stabilization element can be acted upon percutaneously via the insertion tool, in order that the anchoring elements can be connected to one another via the stabilization element.

It is expedient for the data processing unit to determine from the position data of the anchoring elements and, where appropriate, from the data of the positions and orientations of the stabilization element receptacles whether the anchoring elements are connectable to the stabilization element, it being possible for the shape of the stabilization element to be preset in the data processing unit. For example, the shape of the stabilization element can be determined from planning data of the preoperative planning and stored in the data processing unit. The surgeon can, therefore, ascertain in a user-friendly way whether a connection of the anchoring elements to the stabilization element is possible at all.

It is advantageous for the instrumentation to comprise a display unit and for the data processing unit to provide an indication to reposition at least one anchoring element, where appropriate, to change the position and/or the orientation of a stabilization element receptacle of at least one anchoring element. In particular, if the result of the check in the last-mentioned advantageous embodiment is negative, it is then possible to suggest to the surgeon a change in the relative orientation of the anchoring elements and, where appropriate, of the stabilization element receptacles. The surgeon can thereby be assisted in a correct positioning so as to enable connection of the anchoring elements to the stabilization element.

It is expedient for the instrumentation to comprise a plurality of stabilization elements of different shapes, and for the data processing unit to provide information for selection of a stabilization element suitable for connection of the anchoring elements. The instrumentation, therefore, proves to be versatile and easy to handle. In accordance with the indication of the data processing unit, the surgeon can use a suitable stabilization element.

It is advantageous for the instrumentation to comprise a stabilization element shaping device, and for the data processing unit to provide information for the shaping of the stabilization element with the shaping device by a user, or for the data processing unit to control the shaping device for shaping the stabilization element, so that the anchoring elements are connectable to one another via the stabilization element. The shaping device may be a controllable or hand-operated shaping device, for example, a bending device for bending the stabilization element, in particular, in the form of a rod. On the basis of the indication of the data processing unit or of the controlling of the shaping device, it can thereby be ensured that the anchoring elements can be connected to one another via the stabilization element.

The instrumentation preferably comprises an ultrasonic probe which can be coupled to the data processing unit, and ultrasonic image signals of the ultrasonic probe can preferably be represented by the data processing unit on a display unit of the instrumentation. This makes it possible, via the ultrasonic probe, to localize body tissue, for example, vertebral bodies, in particular, their pedicles, with the ultrasonic probe and to visualize these on the display unit. The surgeon can thereby be assisted and instructed in positioning the anchoring elements. The anchoring elements can also be detected with the ultrasonic probe and their relative orientation preferably determined with the ultrasonic probe.

Expediently, a marking device which can be detected by an optical sensor of the sensor unit is coupled to the ultrasonic probe so that the ultrasonic probe can be followed in space. Ultrasonic image signals can thereby be determined and represented in the reference coordinate system.

Advantageously, information relating to a predetermined relative orientation of the two or more anchoring elements can be stored in the data processing unit, and the stored information can preferably be compared to the determined relative orientation of the two or more anchoring elements by the data processing unit. A predetermined relative orientation can, for example, be provided by preoperative planning data originating, for example, from X-ray (specifically CT) images or ultrasonic images. By comparing the, so to speak, desired, predetermined relative orientation of the anchoring elements with the determined actual relative arrangement, it can be easily ascertained whether the anchoring elements are correctly or approximately correctly positioned.

The coupling unit preferably comprises at least one extension element (for example, the access tube or the insertion tool) releasably connectable to an anchoring element or to the stabilization element and a retaining element for retaining the sensor unit on the at least one extension element. The retaining element can be firmly connected or releasably connectable to the at least one extension element. In the state connected to the extension element, the retaining element is in defined relative arrangement in relation thereto, which, in the case of a releasable connection, is reproducible. In a corresponding manner, the sensor unit can be firmly connected or releasably connectable to the retaining element, it being in defined relative arrangement in relation thereto, which, in the case of a releasable connection, is reproducible.

The connection of the sensor unit to the retaining element can be with force and/or positive locking, corresponding to the connection of the retaining element to the at least one extension element and the connection of the at least one extension element to an anchoring element or to the stabilization element.

To simplify explanation of the invention, it will be assumed hereinbelow that where, for example, two extension elements are provided, these have the same length, and, in particular, they may be identical. However, the present invention is not limited to this. Extension elements of different lengths may also be used.

It may be provided that two extension elements are rigidly or articulatedly connected or connectable to one another via the retaining element. For example, the retaining element is pivotably connected by a hinge or ball-and-socket joint to the respective extension element.

Alternatively or additionally, it may be provided that the length of the retaining element is alterable. For example, the retaining element is telescopic.

By changing the length of the retaining element, it is possible to align the extension elements parallel to one another, whereby, as will be explained hereinbelow, a direction from a first anchoring element to a second anchoring element can be easily determined.

For example, it may be provided that the direction from a first anchoring element to a second anchoring element is determinable by the coupling unit being connected to the first anchoring element and the second anchoring element via one extension element, in each case, and the extension elements being connected via a retaining element in such a way that the extension elements are aligned parallel to each other, and that the sensor unit is aligned in a predetermined geometrical relationship to the retaining element. This makes it possible to determine, on the basis of the orientation of the sensor unit the orientation of the retaining element and thereby (on account of the parallel alignment of the extension elements) the direction from the first to the second anchoring element.

It is also conceivable for the direction from a first anchoring element to a second anchoring element to be determinable by the coupling unit being coupled to the first anchoring element and the second anchoring element via one extension element, in each case, and the extension elements being connected via a retaining element in such a way that the angle between the extension elements can be detected by the sensor unit in order to determine the orientation of the imaginary line located opposite the angle, which connects the anchoring elements to each other. The extension elements can be connected to each other at an angle, and the connection can be made via the retaining element on which the sensor unit is held. A triangle is thereby defined with two sides defined by the extension elements and a third side formed by the imaginary line connecting the anchoring elements to each other. In particular, the angle between the extension elements can be determined by the sensor unit and, specifically assuming that the extension elements are of equal length, the direction between the anchoring elements can thereby be determined.

It may, furthermore, be provided that the position of an anchoring element or of the stabilization element is determinable by pivoting the coupling unit with the sensor unit fixed thereto on the anchoring element or on the stabilization element. In the case of the anchoring element, the coupling unit is coupled to a pivotable stabilization element receptacle of the anchoring element. For example, the coupling unit with the sensor unit is moved on the surface of a cone or a spherical surface. The tip of the cone or the center point of the sphere then defines the position of the anchoring element, which can be determined in the reference coordinate system.

Furthermore, it may be provided that the direction from a first anchoring element to a second anchoring element is determinable by the coupling unit being synchronously pivoted relative to the first anchoring element and relative to the second anchoring element, with the coupling unit being coupled to a respective pivotable stabilization element receptacle of the anchoring elements. For example, the coupling unit comprises two extension elements which are rigidly connected to each other via a retaining element, the extension elements being aligned parallel to each other. The sensor unit can thereby be pivoted along a cylinder surface relative to the anchoring elements. This allows the direction between the anchoring elements to be determined. With articulated coupling of the retaining element to the extension elements and their parallel alignment, the sensor unit can be pivoted, for example, in the plane of the extension elements and the retaining element relative to the anchoring elements and the direction between the anchoring elements determined therefrom.

It may, furthermore, be provided that the position of an anchoring element and/or of the stabilization element is determinable from absolute position data (for example, using a GPS sensor) of the sensor unit.

Use of an absolute position sensor also makes it possible to determine absolute position data in position data in the reference coordinate system of the sensor unit and vice versa, whereby a transformation between a world coordinate system and the reference coordinate system is possible.

It is expedient for the instrumentation to comprise a marking device which is movable into different relative positions in relation to the coupling unit with the sensor unit arranged thereon, the marking device being detectable by the sensor unit, in particular, by an optical sensor of the sensor unit, and the position and/or the orientation of the marking device relative to the sensor unit being determinable by the data processing unit. This allows the marking device to be followed in the reference coordinate system of the sensor unit when it moves in space. Position data of objects coupled to the marking device can thereby be determined in a particularly simple way. In particular, it is not necessary to provide an external verification device such as, for example, an external navigation camera, in addition to the sensor unit.

The marking device can preferably be coupled to an anchoring element or to the stabilization element. For example, the marking device can be connected to an extension element of the coupling unit, for example, to the access tube or to the insertion tool. The coupling of the marking device to the anchoring element or to the stabilization element is carried out with a knowledge of the relative arrangement of marking device and anchoring element or stabilization element. The position and/or the orientation of the anchoring element or of the stabilization element can be deduced from following the marking device.

It may be provided that the marking device comprises an optical display unit on which the marking elements can be represented. For example, a further integrated unit in the form of a smartphone, handheld computer or tablet computer is used, which represents on a display unit marking elements which can be detected by the sensor unit.

Alternatively, it may be provided that the marking device comprises marking elements rigidly connected to one another in a marking element arrangement. The marking element arrangement is, for example, a so-called "rigid body".

It is expedient for the instrumentation to comprise a insertion tool which is releasably connectable to the stabilization element, and for the marking device or the sensor unit to be arranged on or be able to be coupled to the insertion tool, the position and/or the orientation of the stabilization element being determinable from the position and/or the orientation of the marking device relative to the sensor unit. For example, the sensor unit is in defined relative orientation in relation to the stabilization element via the coupling unit comprising the insertion tool. The marking device can be coupled to an anchoring element and be in defined relative orientation in relation thereto. When the insertion tool is moved, the position of the stabilization element can be determined in the reference coordinate system relative to the anchoring element referenced via the marking device. Conversely, it may be provided that the sensor unit is coupled to an anchoring element via the coupling unit, and that the marking device is coupled to the insertion tool, with a defined relative arrangement also being provided in each case. As mentioned above, the position of the insertion tool and, therefore, the position of the stabilization element in space can be followed by following the marking device with the sensor unit.

It is expedient for the instrumentation to comprise an indication unit on which indications are displayable for a user for guiding the insertion tool, in order to connect the anchoring elements to one another via the stabilization element. The user can thereby be instructed by the data processing unit as to how the insertion tool is to be moved in order that the stabilization element can be connected to the anchoring elements.

It is advantageous for the instrumentation to comprise identification elements allocated to the anchoring elements, a respective identification element being arranged on or included in an anchoring element, and the identification elements differing from one another, and a detection unit for successive, cable-free detection of the identification elements, for it be determinable by the data processing unit from signals of the detection unit whether the order in which the identification elements are detected matches a preset or presettable sequence, and for a positive or negative indication relating to this to be displayable to a user on an indication unit of the instrumentation. This makes it possible, for example, to assist the user in inserting the stabilization element. Accordingly, it can be provided that the anchoring elements are to be connected to one another in accordance with the preset or presettable sequence via the stabilization element. When inserting the stabilization element, the operator can detect the identification elements successively with the detection unit. The data processing unit can check whether the order of the identification elements matches the sequence. A positive or negative indication can be provided on the indication unit to assist the user. The indication is positive when the identification element matches that which is expected according to the sequence, negative when the identification element deviates from that which is expected according to the sequence. The user can recognize from the indication whether he has "selected" the correct anchoring element for connection to the stabilization element.

The detection of the identification elements preferably takes place by the detection unit approaching the anchoring elements and, therefore, to a certain extent can occur "automatically". A detection signal sent out by the detection unit in the direction of the identification elements and/or a signal sent out or reflected by these in the direction of the detection unit is/are preferably directed for this purpose.

It is advantageous for the identification elements to be RFID tags or optical identification elements and to be detectable by means of RFID technology or optically by the detection unit, this being configured as RFID reader or optical detection unit.

It may be provided that the sequence of the data processing unit is preset ex works. The order in which the anchoring elements are to be connected can already be registered in the data processing unit.

Alternatively or additionally, the sequence of the data processing unit can be preset by the user by successive detection of the identification elements. For example, the user can successively detect the identification elements before or after implantation of the anchoring elements and register the sequence in which the stabilization element is to be connected thereto.

It may be provided that the identification elements can all be detected immediately after one another with the detection unit in order to transmit the sequence to the data processing unit.

Alternatively or additionally, it may be provided that between detecting the identification elements in order to preset the sequence in the data processing unit, a position of the respective anchoring element or relative positions of the anchoring elements in relation to one another are determined in one of the ways described hereinabove or hereinbelow.

The indication unit may be an optical indication unit and, in particular, comprise an image display. It is also conceivable for the optical indication unit to comprise light-emitting elements, e.g., light-emitting diodes. For example, a green light-emitting element is provided for indicating a correct order of detection and a red light-emitting element for indicating an incorrect order of detection.

The indication unit may alternatively or additionally be or comprise an acoustic indication unit which, for example, comprises a loudspeaker for emitting different sounds for positive or negative indication.

Alternatively or additionally, it may be provided that the indication unit is or comprises a tactile indication unit. Depending on positive or negative indication, the indication unit can, for example, provide different vibrations. This is advantageous, for example, when the indication unit is integrated in a tool, for example, an insertion tool for the stabilization element.

The detection unit, and likewise the indication unit, can be separate from the data processing unit and the sensor unit.

In a different implementation, it may be provided that the detection unit is integrated in or included in the data processing unit or in the sensor unit. In particular, the detection unit can be arranged in the same housing with the data processing unit or the sensor unit. Handling of the integrated unit is user-friendly for the surgeon.

It may be provided that the indication unit is integrated in or included in the data processing unit. The indication unit may, in particular, be the aforementioned indication unit which forms an integrated unit with the sensor unit and the data processing unit.

The detection unit can be arranged on a tool, in particular, on an insertion tool for the stabilization element or on a marking device (for example, a rigid body) of the instrumentation or be included therein.

The instrumentation can comprise a carrier for the detection unit and/or the indication unit. The carrier is preferably constructed such that it can be arranged and carried on a user's body, in particular, under sterile clothing.

In an advantageous implementation, it may be provided that the instrumentation includes a bracelet comprising the detection unit and/or the indication unit. For example, the surgeon wearing the bracelet can approach the anchoring elements with his hand. Their identification elements can be detected by the detection unit which, in this case, is preferably an RFID reader. An indication unit including, for example, an image display or light-emitting elements can be arranged on the bracelet.

It is expedient if in dependence upon a signal of the detection unit relating to the detection of an identification element, the sensor unit can be provided with an activation signal or a reset signal, in order to activate or reset the sensor unit. This is, for example, expedient when presetting the sequence in the data processing unit, as explained hereinabove. When the identification element is detected, the sensor unit can be reset in order to reduce possible measuring errors when subsequently determining the position of the anchoring element. A possible measuring error is, for example, a drift of a sensor, e.g., an initial sensor used to detect the position of the anchoring element. In this way, the accuracy when determining the relative positions of the anchoring elements can be increased. Energy for using the sensor unit can be saved by specific activation and deactivation of the sensor unit in dependence upon a signal of the detection unit.

To save energy for the detection unit, it is advantageous for it to be selectively activatable and/or deactivatable by means of an activation signal. It may be provided that the detection unit is only activated during the surgical procedure. The lifespan of the detection unit, if it is battery-operated, can thereby be increased. The detection unit can be activated at the start of the procedure and subsequently deactivated. It is also possible for the user to activate and/or deactivate the detection unit several times during the procedure.

The activation signal can be sent to the detection unit wirelessly, for example, via a wireless switch-on or switch-off pulse. The pulse is provided, for example, via a Bluetooth low-energy radio module.

Alternatively or additionally, it may be provided that the detection unit comprises an acceleration sensor for providing the activation signal in dependence upon a movement of the detection unit. The user can activate or deactivate the detection unit by suitable movement.

As mentioned at the outset, the invention also relates to a method. The object set at the outset is accomplished, in accordance with the invention, by a method in which one of the aforementioned instrumentations is used, which comprises two or, in particular, more anchoring elements for anchoring on body tissue and a stabilization element via which the two or more anchoring elements are connectable, wherein the sensor unit is percutaneously selectively coupled to at least one anchoring element or to the stabilization element via the coupling unit, and the position of the anchoring elements relative to one another and/or the position of at least one anchoring element relative to the stabilization element is determined by a data processing unit from sensor signals of the sensor unit.

The advantages mentioned in connection with the explanation of the instrumentation in accordance with the invention and advantageous embodiments thereof can also be achieved by using the method. In this regard, reference is to be had to the explanations given hereinabove.

Advantageous embodiments of the method in accordance with the invention result from advantageous embodiments of the instrumentation in accordance with the invention. Their features can be used to define advantageous embodiments of the method, and, therefore, reference is made to statements made hereinabove in order to avoid repetitions.

FIG. 1 shows an advantageous embodiment of an instrumentation in accordance with the invention denoted by reference numeral 10. The instrumentation 10 comprises, in the present case, a surgical fixation system 12 for stabilization of vertebrae 14. For this purpose, the fixation system 12 comprises anchoring elements 18, in the present case configured as bone screws, and, in particular, polyaxial screws 20. The polyaxial screws 20 are, in particular, pedicle screws, which can be screwed into pedicles of the vertebrae 14.

The polyaxial screws include screw heads 22, which form a respective stabilization element receptacle 24 for a stabilization element 26 of the fixation system 12. The screw heads 22 are pivotable relative to threads 28 of the polyaxial screws 20 via an, in particular, spherical joint connection. With the screw heads 22 remaining in the same position, their orientation in space is thereby changed. A respective direction of insertion 30 of a screw head 22 in which the stabilization element 26 can be inserted into the screw head 22 is thereby also changed.

In the present case, the stabilization element 26 is a rod 32 which can be passed through the screw heads 22 and in a manner known per se fixed in a clamped manner thereto. This allows the polyaxial screws 20 to be connected to one another via the rod 32 and the vertebrae 14 to be stabilized.

The fixation system 12 further comprises an insertion tool 34 to which the rod 32 can be firmly coupled. The rod 32 can be percutaneously moved via the insertion tool 34. The coupling of the rod 32 is such that with the position of the insertion tool 34 in space known, the position of the rod 32, in particular, of a rod end 341 of the rod 32, is known and determined.

The fixation system 12 further comprises at least one extension element 36, in the present case, in the form of an access tube 38. The access tube 38 can be releasably connected to the screw head 22, the relative arrangement of the screw head 22 and the access tube 38 being known and reproducible. This allows the position of the screw head 22 and, in particular, its insertion opening for determining the direction of insertion 30 to be deduced from the position of the access tube 38. The screw head 22 can be acted upon percutaneously through the access tube 38, for example, in order to clamp the rod 32.

In the present case, a plurality of access tubes 38 are provided, and each polyaxial screw 20 can have its own access tube 38 allocated to it.

The instrumentation 10 further comprises an integrated, handheld and portable data processing unit 40, which may, for example, be a handheld computer 42, a smartphone or a tablet computer. The computer 42 is releasably connectable to a respective access tube 38 via a retaining element 44. The connection is made in such a way that both the relative arrangement of the computer 42 in relation to the retaining element 44 and the relative arrangement of the retaining element in relation to the access tube 38 are known and reproducible. A known and reproducible relative arrangement of the computer 42 in relation to the screw head 22 can thereby also be ensured. The connection of the computer 42 to the access tube 38 via the retaining element 44 can be made with force and/or positive locking and manually and, in particular, without a tool. The retaining element 44 can also be released from the computer 42.

The integrated data processing unit 40 comprises in a manner known per se a microprocessor, not shown, an integrated indication unit 46 with an optical display unit in the form of a screen 48 and with a loudspeaker 50.

Also integrated in the data processing unit 40 is a sensor unit 52. The sensor unit 52 comprises, in particular, a plurality of sensors and on the basis of their measurements provides sensor signals which can be evaluated by the data processing unit 40. In the present case, an absolute position sensor, for example, a GPS sensor, an inclination sensor for determining an inclination and/or a change in the inclination of the computer 42, a compass sensor (in particular, in the form of a magnetic field sensor), an inertial sensor for determining an acceleration and/or rotation rate of the computer 42 and an optical sensor are preferably provided as sensors.

Figure 7:
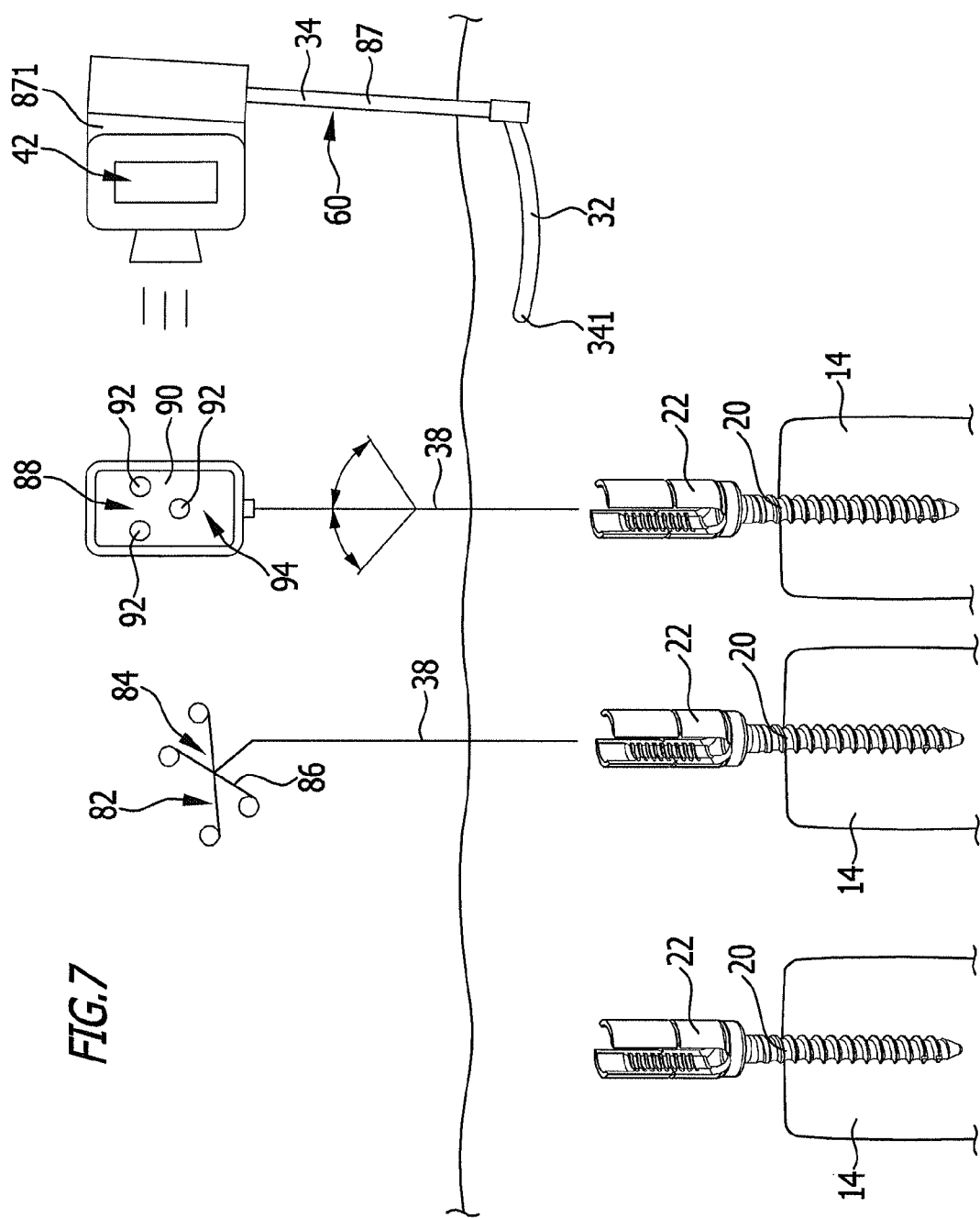
FIG. 7 shows schematically the use of the instrumentation from FIG. 1 when inserting a stabilization element of the instrumentation.

The optical sensor is configured, in particular, as a digital camera 54, which is shown schematically in FIGS. 7 and 8.

The sensor unit 52 defines a reference coordinate system in which, as explained hereinbelow, the position and/or orientation of the screw heads 22 and, therefore, of the polyaxial screws 20 can be determined. The directions from a screw head 22 of a polyaxial screw 20 to the screw head 22 of a further polyaxial screw 20 can also be determined. As a result, the relative arrangement of the screw heads 22 can thereby be determined percutaneously, whereby the rod 32 can be percutaneously threaded through the screw heads 22 in a surgeon-friendly and patient-friendly manner and connected to the polyaxial screws 20.

The instrumentation 10 further comprises a stabilization element shaping device 56 in the form of a bending device 58. The bending device 58 is controllable by the computer 42 in order that a rod can be bent in a predetermined shape.

Alternatively or additionally, the bending device 58 is manually actuatable. On the basis of information provided by the computer 42, a surgeon can impart a predetermined shape to the rod.

The coupling unit 60 of the instrumentation 10 includes the access tubes 38 and the retaining element 44. The computer 42 can be selectively connected to the polyaxial screws, in particular, to their screw heads 22 via the coupling unit 60. This allows the computer 42 to be connected, in particular, successively to polyaxial screws 20 and position and/or orientation data of the screw heads 22 to be selectively and successively determined with the computer 42.

It may, of course, be provided that the fixation system 12 comprises more than only two anchoring elements 18 and extension elements 36. Beyond the retaining element 44, the coupling unit 60 may comprise further and/or different kinds of retaining elements, as will be explained in more detail hereinbelow.

With reference, in particular, to FIGS. 2 to 6, it will be explained by way of example hereinbelow how the position and/or the orientation of the screw heads 22 and directions between the screw heads 22 can be determined.

In principle, it is conceivable for absolute position data to be determined with the sensor unit 52. On the basis of the known positional arrangement of the computer 42 in relation to a respective screw head 22, absolute position data can then be determined in the absolute coordinate system.

Figure 2:
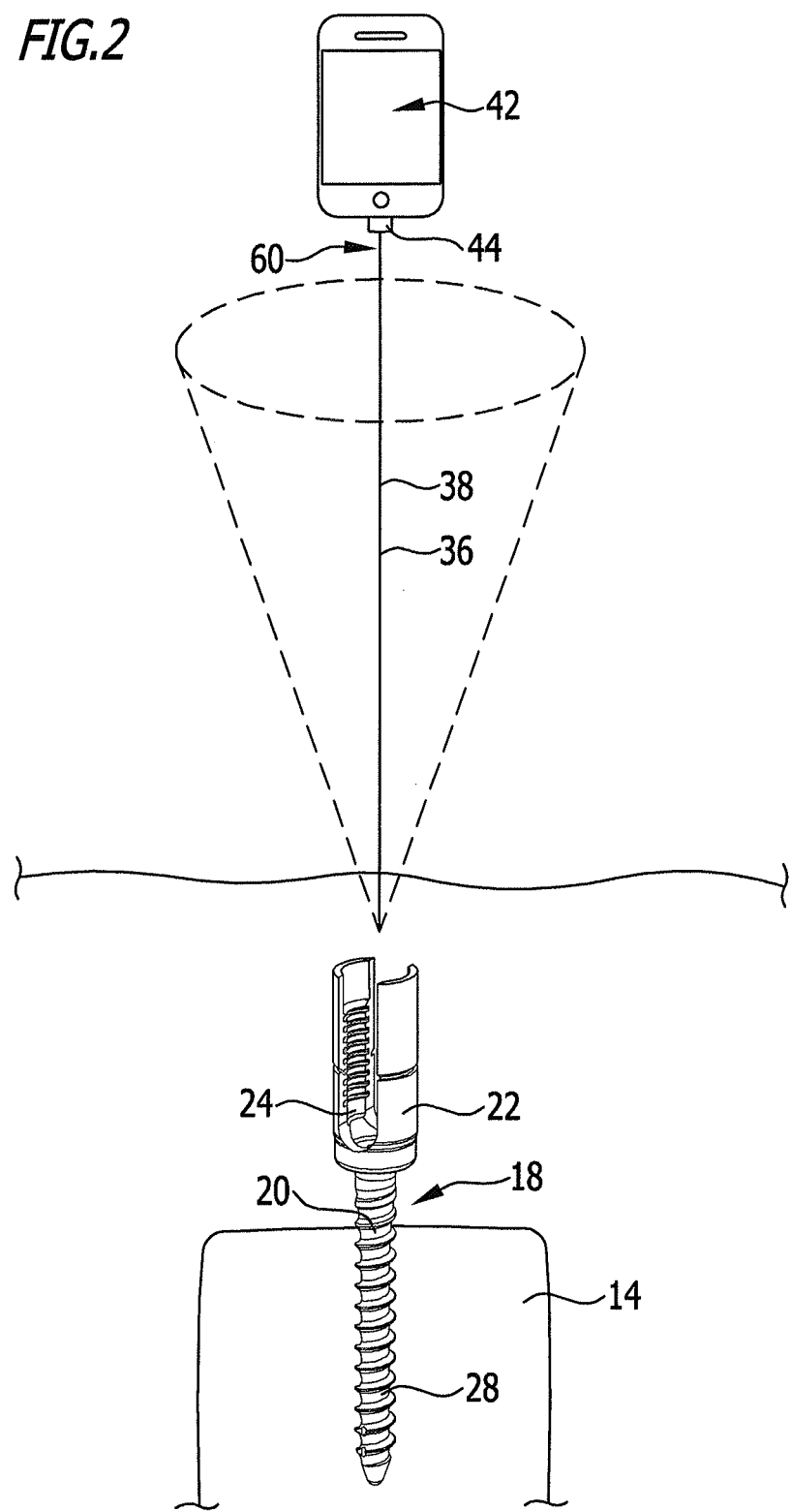
FIG. 2 shows schematically the pivoting of a data processing unit relative to an anchoring element of the instrumentation from FIG. 1.

In FIG. 2 it is shown schematically how the computer 42, by pivoting the coupling unit 60 to which it is attached, can determine the position of the screw head 22 on the polyaxial screw 20 in the reference coordinate system. For example, the computer 42 is pivoted on the surface of a cone or the surface of a sphere, with the tip of the cone or the center point of the sphere thereby defining the position of the screw head 22. The direction of insertion 30 can also be determined on the basis of the known positional relationship of the computer 42 to the screw head 22.

In the variant in accordance with FIG. 2, in particular, an inclination sensor of the sensor unit 52 is used. A translation of the computer 42 can be determined by an inertial sensor of the sensor unit 52, and by successively connecting the computer 42 to the screw heads 22 a polygonal chain can thereby be defined in the reference coordinate system.

Figure 3:
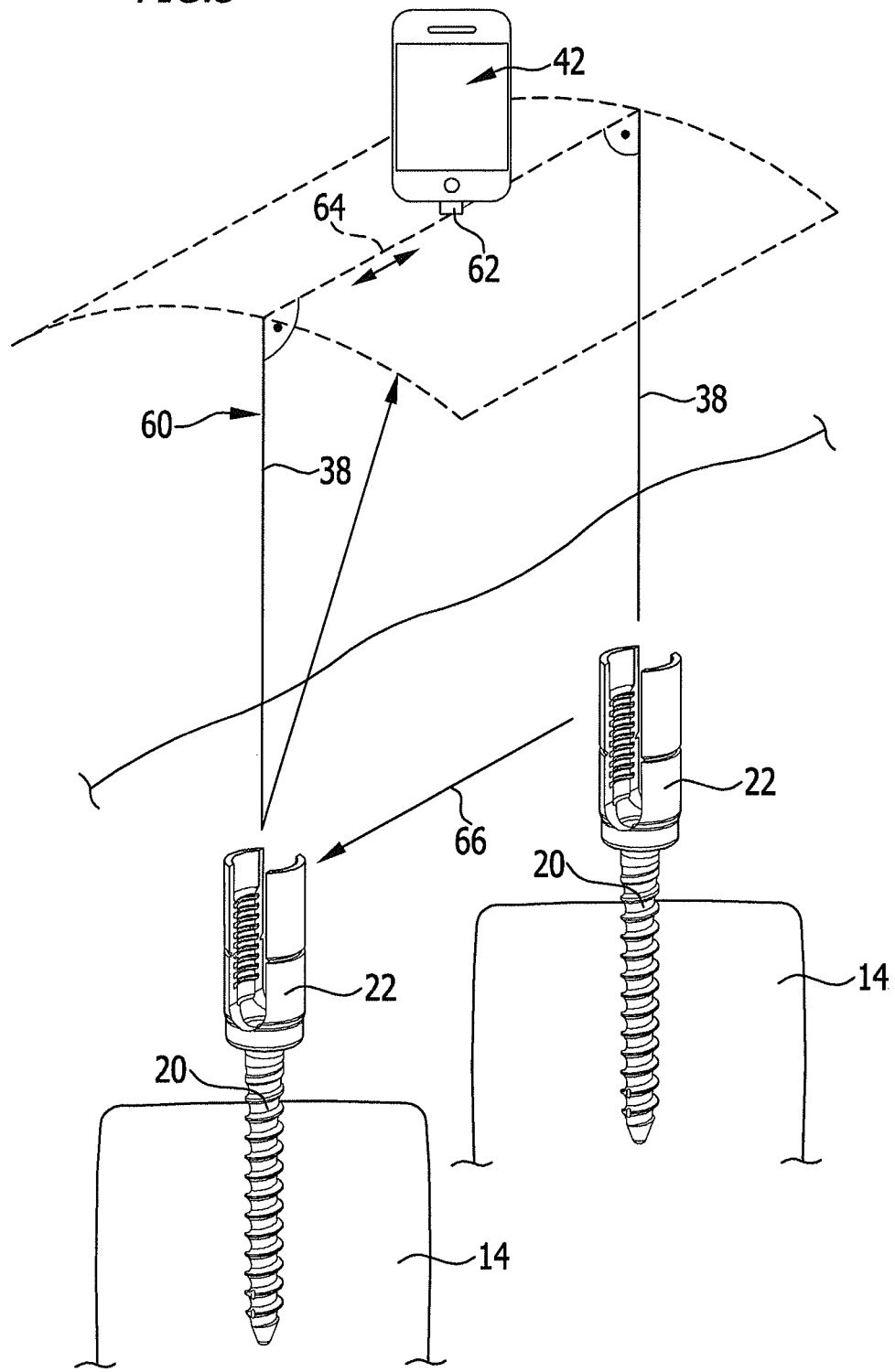
FIG. 3 shows schematically the pivoting of the data processing unit relative to two anchoring elements.

In the variant in accordance with FIG. 3, a retaining element 62 is provided, which is configured in sections like the retaining element 44, which forms a retaining section of the retaining element 62. The retaining element 62 further comprises a connecting section 64. The connecting section 64 is firmly connected to the access tubes 38, for example, to their ends facing away from the screw heads 22 and, in particular, outside of the patient's body.

In the variant in accordance with FIG. 3, the computer 42 is pivoted on the surface of a cylinder at the polyaxial screws 20 via the coupling unit 60. In particular, using an inclination sensor, it is possible to deduce therefrom the orientation of the connecting section 64, from which a direction 66 from one polyaxial screw 20 to the next polyaxial screw 20 results. For this purpose, it is advantageous for the connecting section 64 to be variable in length in order that the access tubes 38 can be aligned parallel to one another.

The directions from one polyaxial screw 20 to the next polyaxial screw can now be determined successively. The positions of the screw heads 22 can be determined, for example, as explained hereinabove, using an inertial sensor.

Figure 4:
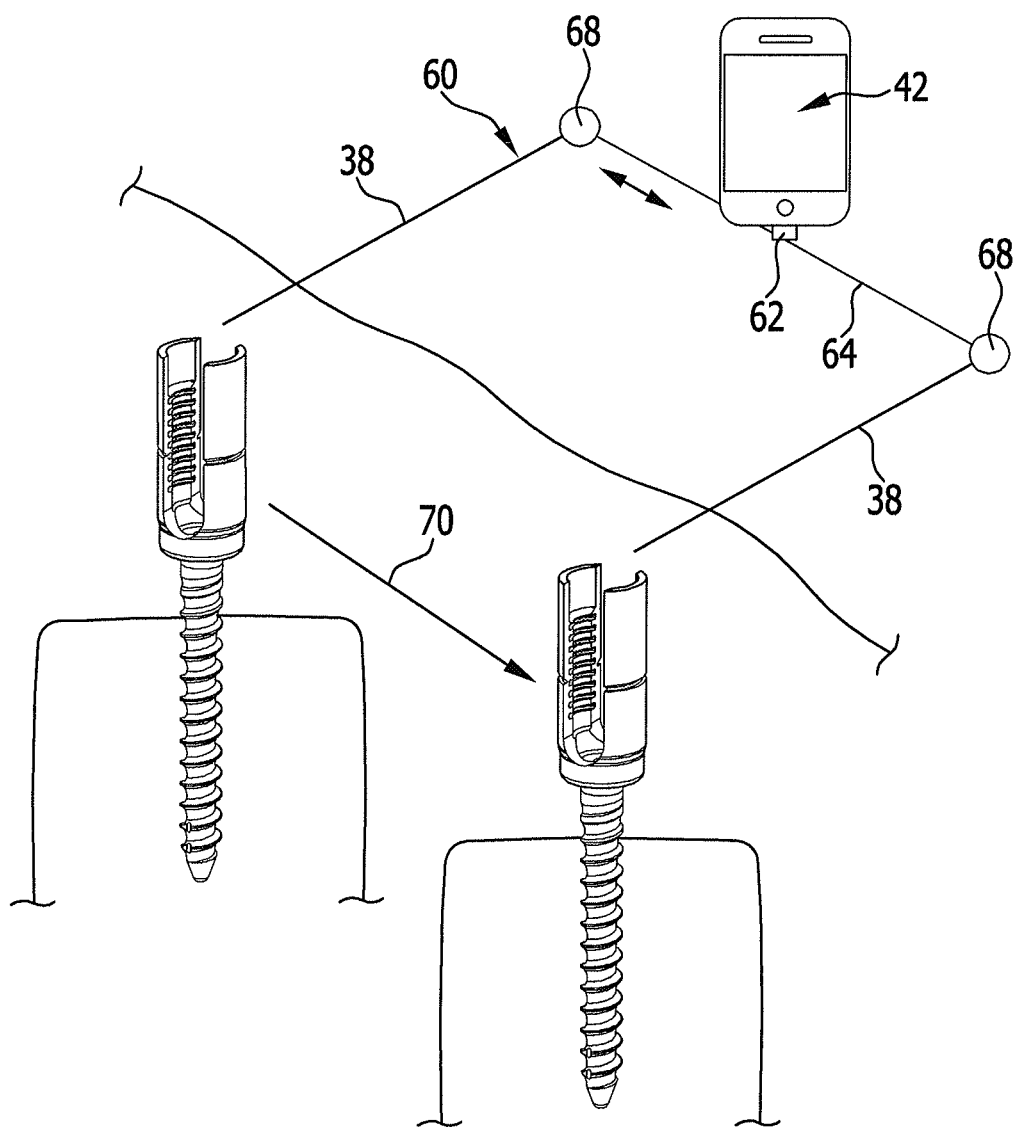
FIG. 4 shows schematically the pivoting of the data processing unit relative to two anchoring elements in a different way.

In the variant in accordance with FIG. 4, the connecting section 64 is articulatedly connected to the access tubes 38. For this purpose, joints 68 are provided, for example, hinge or ball-and-socket joints. In particular, pivoting of the computer 42 in a plane defined by the access tubes 38 and the connecting section 64 is possible. In this case, too, the connecting section 64 is preferably variable in length so as to enable parallel alignment of the access tubes 38.

Using, in particular, an inclination sensor and an inertial sensor, the movement of the computer 42 is determined, and the orientation of the connecting section 64 and, consequently, a direction 70 from a first polyaxial screw 20 to the next polyaxial screw 20 are thereby determined.

For further determination of the position and orientation of the screw heads 22, the procedure as explained hereinabove may, for example, be used.

Figure 5:
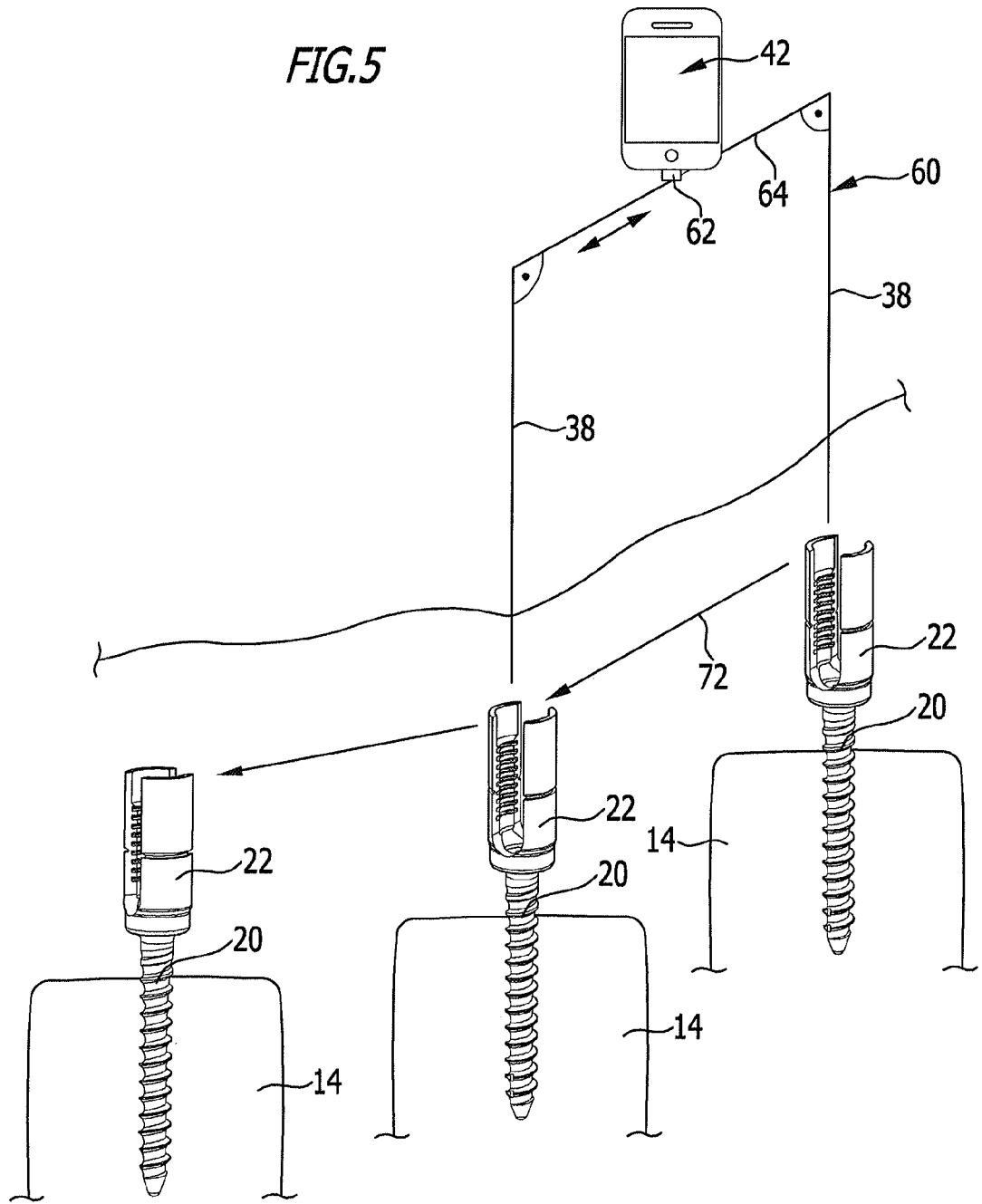
FIG. 5 shows schematically the static coupling of the data processing unit to two anchoring elements.

In the variant in accordance with FIG. 5, a static determination of the direction 72 of two polyaxial screws 20 following one another is used. As in the variant in accordance with FIG. 3, the connecting section 64 is rigidly connected to the access tubes 38. The connecting section 64 is preferably variable in length in order that the access tubes 38 are aligned parallel to one another.

Using, in particular, an inclination sensor and a compass sensor, the direction 72 can thereby be determined in the reference coordinate system.

For further determination of position and/or orientation of the screw heads 22, the procedure as explained hereinabove may be used.

In the variants in accordance with FIGS. 3 to 5, it may be provided that the length of the connecting section 64 can be determined. This may be done by, for example, using an optical sensor of the sensor unit 52. By determining the length of the connecting section 64, it is possible to also determine from the information relating to the directions 66, 70 or 72 the distance of the polyaxial screws 20 from one another in the reference coordinate system.

Figure 6:
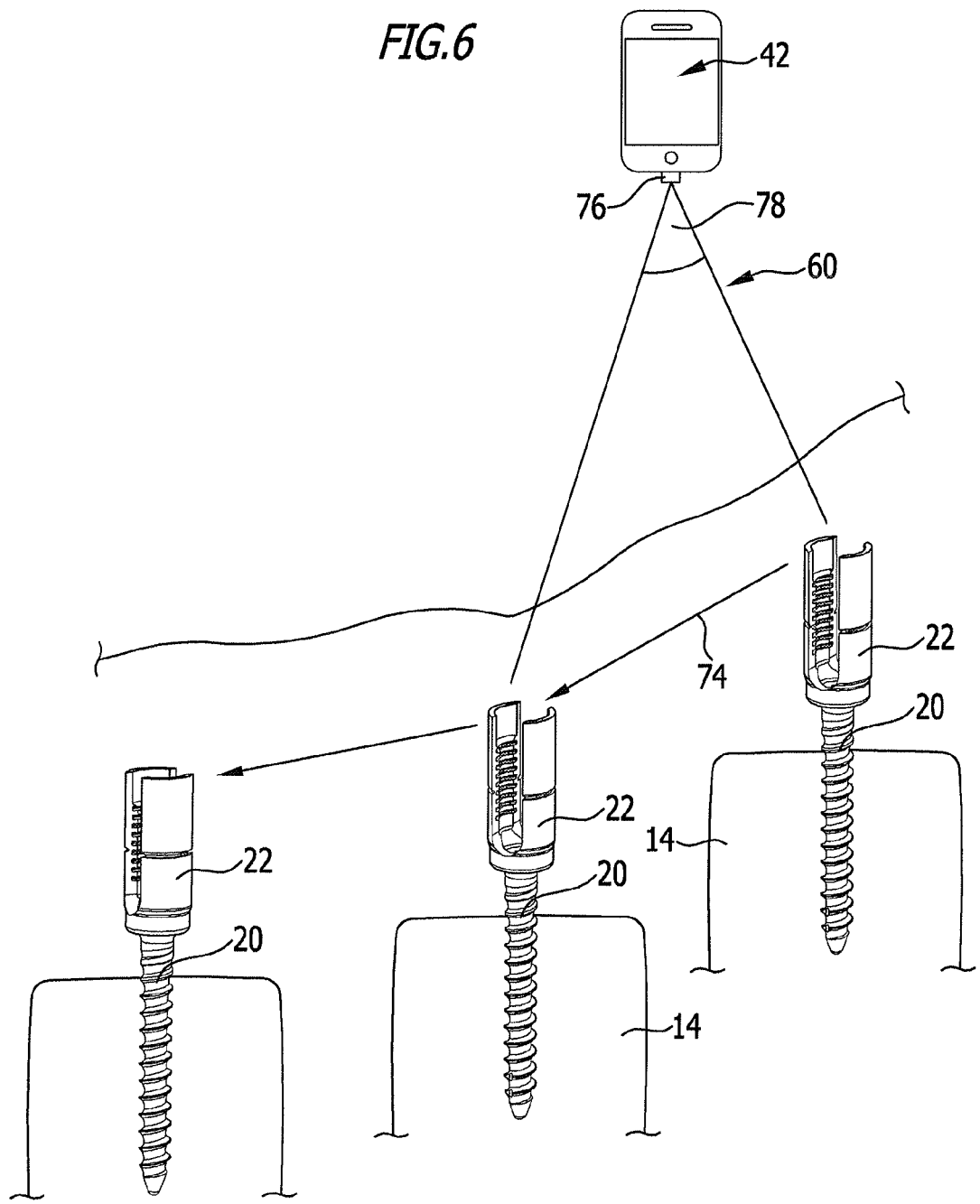
FIG. 6 shows schematically the static coupling of the data processing unit to two anchoring elements in a different way.

A further static measurement of a direction 74 between two polyaxial screws 20 is shown in the variant in accordance with FIG. 6. Here a retaining element 76 of the coupling unit 60 is used, which connects the computer 42 to the access tubes 38. The access tubes 38 thereby define two sides of an equilateral triangle, the third side of which is defined by an imaginary line connecting the screw heads 22 to one another. On the basis of the known positional relationship of the computer 42 relative to the access tubes 38, in which the geometry of the retaining element 76 is incorporated, an angle 78 between the access tubes 38 can be determined using, in particular, an inclination sensor and a compass sensor. The direction 74 can be deduced from the angle 78.

The access tubes 38 can also be movably connected to one another by the retaining element 76 so that they can be pivoted at the respective screw head 22, thereby changing the angle 78. In this case, too, it is possible to deduce the angle 78 and, therefore, the direction 74 from the data, in particular, of the inclination and compass sensors.

To determine the further position and/or orientation data of the screw heads 22, the procedure as explained hereinabove may, for example, be used.

The data processing unit 40 can instruct the surgeon, in particular, via the screen 48, to record the position and/or orientation data of the polyaxial screws 20, in particular, of their screw heads 22. It is, for example, possible to proceed in one of the ways explained with reference to FIGS. 2 to 6 or, as mentioned before, an absolute position sensor can be used to establish a relationship to a world coordinate system.

On the basis of the determined relative arrangement of the polyaxial screws 20, the computer 42 can determine whether the screw heads 22 are connectable to the rod 32 at all. The shape of the rod 32 can be provided by the computer 42 and stored therein.

The computer 42 can also provide information on the basis of which a user can bend a rod into a shape with the bending device 58 so that the polyaxial screws 20 can be connected to one another. Alternatively or additionally, the bending device 58 can be controlled in a suitable manner by the computer 42.

The computer 42 can also provide information for selecting a suitable rod from a plurality of existing rods (not shown) of different shape so as to enable the polyaxial screws 20 to be connected.

The computer 42 can provide information for repositioning at least one polyaxial screw 20 or at least one screw head 22 in order that the polyaxial screws 20 can be connected to one another via the rod 32.

The relative arrangement of the polyaxial screws 20, as determined from the signals of the sensor unit 52, can be compared with preoperatively provided information relating to a desired relative arrangement of the polyaxial screws 20 so as to ensure that the preoperative objective of the operation will be achieved.

The instrumentation 10 comprises an ultrasonic probe 80 which can be operatively coupled to the computer 42 so as to transmit signals. Ultrasonic image signals can be represented on the screen 48. The ultrasonic probe 80 can thereby be used to assist in locating the vertebrae 14, in positioning the polyaxial screws 20 and in inserting the rod 32. The ultrasonic probe 80 can be provided with a marking device, not shown in the drawings, which, in particular, can be detected by an optical sensor of the sensor unit 52. Ultrasonic image data can thereby be determined and represented in the reference coordinate system.

To insert the rod 32, reference will be made hereinbelow, in particular, to FIG. 7.

The instrumentation comprises a marking device 82 which can be coupled to a polyaxial screw 20. For this purpose, an access tube 38, for example, can be used, to which the marking device 82 can be attached in a defined relative arrangement in a reproducible manner. Alternatively, an independent coupling unit can be used.

In the present case, a so-called "rigid body" 84 defining a rigid marking element arrangement 86 is used, for example, as marking device 82.

The coupling unit 60 comprises the insertion tool 34 for coupling the computer 42 to the rod 32. The insertion tool 34 is an extension element 87. The computer 42 can be releasably attached in a defined relative arrangement to the insertion tool 34 via a retaining element 871 of the coupling unit 60. The relative arrangement of the rod 32 and the computer 42, in particular, of the sensor unit 52 and the rod end 341 is known.

The relative orientation of the marking device 82 and the computer 42 can be changed. For example, the marking device 82 is connected to a polyaxial screw 20, and the insertion tool 34 and, therefore, the rod 32 are moved in order to insert the rod 32 percutaneously. The relative movement of the marking device 82 and the computer 42 can be followed by means of an optical sensor of the sensor unit 52, and the movement of the respective screw head 22 thereby deduced in the reference coordinate system. With the relative orientation of the screw heads 22 known, this allows the rod 32 to be guided percutaneously in a manner which is user-friendly and gentle on the patient through the screw heads 22 in order to connect the polyaxial screws 20 to one another.

Conversely, it can, of course, also be provided that the marking device 82 is fixed on the insertion tool 34 in a defined relative arrangement in relation to the rod 32 and that the computer 42 is coupled to a polyaxial screw 20.

In particular, it is possible to pass the rod 32 successively through the screw heads 22 by the marking device 82 being successively connected to the polyaxial screws 20 and followed in space or by the computer 42 being successively connected to the polyaxial screws 20 and the marking device 82 being followed on the insertion tool 34. More specifically, this is also possible without the position of the screw heads 22 being previously determined in the reference coordinate system, as explained by way of example hereinabove.

As an alternative or in addition to the marking device 82, it is also possible to provide a marking device 88 with an optical display unit 90 on which marking elements 92 are shown. For example, the marking device 88 is connected to a respective polyaxial screw 20 via the retaining element 44 and an access tube 38.

It may also be provided that the marking device 88 is formed by a data processing unit 94. The data processing unit 94 and the data processing unit 40 can, in particular, also transmit position and orientation data in the reference coordinate system and in the world coordinate system, for example, by radio communication. For this purpose, it is possible for a respective absolute position sensor to be used, and use of the digital camera 54 can thereby be eliminated.

The marking device 82 and/or the marking device 88 can also be used to determine position and/or orientation data of the polyaxial screws 20, in particular, their screw heads 22. This is shown schematically in FIG. 8. In this case, it is, for example, provided that the computer 42 is coupled via the coupling unit 60 to a polyaxial screw 20. The marking device 82 can be successively coupled to the further polyaxial screws 20. The relative orientation in relation to the computer 42 can be detected, in particular, by the digital camera 54 and the relative arrangement of the polyaxial screws 20 thereby determined.

The same applies accordingly to the marking device 88, which can be used additionally or alternatively.

A further possibility of detecting the position of a screw head is not shown in the drawings. In this case, the digital camera 54 is coupled to an endoscope which is inserted, for example, through an access tube 38. A characteristic structure of the polyaxial screw 20, for example, of the screw head 22 can be detected with the endoscope, and its position thereby determined in the reference coordinate system.

FIG. 9 shows schematically vertebrae 14 with bone screws 20, for example, polyaxial screws fixed thereto. The bone screws 20 each comprise an identification element 100. These are allocated to the bone screws 20 and allow their clear identification within the instrumentation 10.

In the present case, the identification elements 100 are configured as RFID tags 102. Each RFID tag 102 has an identification. In the drawings, these are shown by way of example as "GK", "GH" and "FU". The identification could also be different.

The instrumentation 10 comprises a detection unit 104 for detecting the identification elements 100. This is an RFID reader 106. The identification of a respective RFID tag 102 can be detected with the RFID reader 106 when it is located in the vicinity of the corresponding RFID tag 102. The RFID reader 106 is preferably coupled in a cable-free manner to the computer 42, for example, by radio communication, and can transmit signals relating to the detected identifications of the RFID tags 102 to it.

The instrumentation 10 further comprises an indication unit 108 which is coupled to the computer 42 and, for example, can be optically and/or acoustically and/or haptically configured. In the present case, the indication unit is, for example, configured as display unit 110 or includes such a display unit. The display unit 110 can comprise light-emitting elements such as light-emitting diodes and/or an image display.

The indication unit 46 can be used as an alternative or in addition to the indication unit 108.

The detection unit could also be integrated in the computer 42.

The instrumentation 10 can preferably comprise a common carrier for the RFID reader 106 and the display unit 110, which can be conveniently carried on the surgeon's body, in particular, under sterile clothing. In the advantageous embodiment shown in the drawings, the carrier is a bracelet 112. The bracelet is attached to a schematically shown forearm 114 of the surgeon, for example, near the wrist.

A sequence of the RFID tags 102 can be preset in the computer 42. In particular, this can be understood as information as to the order in which the bone screws 20 including the REID tags 102 are to be connected to the rod 32 by the surgeon in order to implant the fixation system 12 as desired. In other words the sequence of the RFID tags 102 and, therefore, of the bone screws 20 is registered on the basis of the identifications in the computer 42.

The identifications of the RFID tags 102 can be registered in the computer 42 ex works. Alternatively or additionally, the registration can be carried out, for example, before or during implantation of the bone screws 20. It may be provided that the identifications of the RFID tags 102 are registered when determining the position and the relative positions of the bone screws 20 in one of the ways explained hereinabove. Here it is possible to register all of the RFID tags 102 one immediately after the other or in alternation with determination of the position of one of the bone screws 20.

To detect the respective identification, the surgeon can approach the respective bone screw 20 with his forearm 114 until the identification of its RFID tag 102 is detected by the RFID reader 106 and sent to the computer 42 via a signal. This happens, to some extent, automatically, upon approaching the bone screw 20.

The surgeon can be instructed via the indication units 46 and/or 108 to detect the identifications.

In the present example, the sequence "FU-GH-GK" of identifications is preset and stored in the computer 42. The respective bone screws 20 are to be connected in this order When inserting the rod 32, it is desirable to ensure that the rod 32 is guided to the right bone screw 20. For this, the identifications of the RFID tags 102 can be successively detected by the surgeon and transmitted to the computer 42. The computer checks whether the order matches the registered sequence. By way of an indication, the surgeon receives feedback as to whether the correct bone screw 20 is "aimed at" with the rod 32.

For example, the surgeon approaches the first bone screw 20 with his forearm 114 and detects its identification "FU" via the RFID reader 106. The computer determines that the first identification "FU" matches the beginning of the registered sequence. A positive indication is displayed at the display unit 110. The surgeon inserts the rod 32 into the screw head of the first bone screw 20.

The surgeon then approaches the second bone screw 20 with his forearm 114 and detects its identification "GH" via the RFID reader 106. The computer determines that the second identification "GH" matches the continuation in accordance with the registered sequence. A positive indication is displayed (e.g. green light-emitting diode) at the display unit 110. The surgeon inserts the rod 32 into the screw head of the second bone screw 20.

The surgeon thereupon approaches the third bone screw 20 with his forearm 114 and detects its identification "GK" via the RFID reader 106. The computer determines that the third identification "GK" matches the further continuation in accordance with the registered sequence. A positive indication is displayed at the display unit 110. The surgeon inserts the rod 32 into the screw head of the third bone screw 20.

If, on the other hand, in the step before the last, the bone screw 20 with the identification "GK" is regarded by the surgeon as the supposedly next one, he approaches this (third) bone screw 20 with his forearm 114 and detects its identification "GK" via the RFID reader 106. The computer determines that the identification "GK" does not match the continuation in accordance with the registered sequence. A negative indication is displayed (e.g. red light-emitting diode) at the display unit 110. The surgeon knows from this that he must select another bone screw.

In this way, the handling of the instrumentation 10 and the implantation of the fixation system 12 are made considerably easier for the surgeon by the surgical procedure being assisted. This is to be understood, in particular, in view of a percutaneous implantation. Differently from the situation shown schematically in the drawings, the position in which the next bone screw 20 to be connected to the rod 32 is located is often not obvious in practice, in particular, when a plurality of and/or closely positioned bone screws 20 are present.

The invention claimed is:

1. Medical instrumentation, comprising two or more anchoring elements for anchoring on body tissue and a stabilization element via which the two or more anchoring elements are connectable, and comprising a sensor unit, a coupling unit for percutaneous selective coupling of the sensor unit to at least one anchoring element or to the stabilization element, and a data processing unit which determines from sensor signals of the sensor unit at least one of the position of the anchoring elements relative to one another, and the position of at least one anchoring element relative to the stabilization element, the data processing unit generating position data based on the sensor signals of the sensor unit and the at least one of the position of the anchoring elements relative to one another and the position of at least one anchoring element relative to the stabilization element being defined in a reference coordinate system defined by the sensor unit.

2. Instrumentation in accordance with claim 1, wherein the two or more anchoring elements comprise a respective stabilization element receptacle into which the stabilization element is insertable in a direction of insertion, and wherein the data processing unit determines from the sensor signals of the sensor unit the relative position of the stabilization element receptacles and the orientation of the respective stabilization element receptacle, with the coupling unit being positionable in a defined position and orientation in a reproducible manner at the stabilization element receptacle.

3. Instrumentation in accordance with claim 1, wherein the sensor unit and an indication unit of the instrumentation are integrated in the data processing unit, and wherein this is portable in the form of a smartphone, handheld computer or tablet computer.

4. Instrumentation in accordance with claim 1, wherein the sensor unit comprises at least one of the following sensors:
   a position sensor;
   an inclination sensor;
   a compass sensor;
   an inertial sensor; and
   an optical sensor.

5. Instrumentation in accordance with claim 1, wherein the anchoring elements are bone screws and wherein the stabilization element is a rod.

6. Instrumentation in accordance with claim 1, wherein the coupling unit comprises or forms an access tube which is releasably connectable to an anchoring element in the form of a bone screw and is positionable in a defined position and orientation in a reproducible manner at a stabilization element receptacle of the bone screw, or wherein the coupling unit comprises or forms an insertion tool which is releasably connectable to the stabilization element, the stabilization element being attachable in a defined position and orientation to the insertion tool.

7. Instrumentation in accordance with claim 1, wherein the data processing unit determines from the position data of the anchoring elements whether the anchoring elements are connectable to the stabilization element, it being possible for the shape of the stabilization element to be preset in the data processing unit.

8. Instrumentation in accordance with claim 1, wherein the instrumentation comprises a display unit, and wherein the data processing unit provides an indication to reposition at least one anchoring element or to change at least one of the position and the orientation of a stabilization element receptacle of at least one anchoring element.

9. Instrumentation in accordance with claim 1, wherein the instrumentation comprises a plurality of stabilization elements of different shapes, and wherein the data processing unit provides information for selection of a stabilization element suitable for connection of the anchoring elements.

10. Instrumentation in accordance with claim 1, wherein the instrumentation comprises a stabilization element shaping device, and wherein the data processing unit provides information for the shaping of the stabilization element with the shaping device by a user, or that the data processing unit controls the shaping device for shaping the stabilization element, so that the anchoring elements are connectable to one another via the stabilization element.

11. Instrumentation in accordance with claim 1, wherein the coupling unit comprises at least one extension element releasably connectable to an anchoring element or to the stabilization element and a retaining element for retaining the sensor unit on the at least one extension element.

12. Instrumentation in accordance with claim 1, wherein the position of at least one of an anchoring element and of the stabilization element is determinable from absolute position data of the sensor unit.

13. Instrumentation in accordance with claim 1, wherein the instrumentation comprises a marking device which is movable into different relative positions in relation to the coupling unit with the sensor unit arranged thereon, the marking device being detectable by the sensor unit and at least one of the position and the orientation of the marking device relative to the sensor unit being determinable by the data processing unit.

14. Instrumentation in accordance with claim 13, wherein the marking device is adapted to be coupled to an anchoring element or to the stabilization element.

15. Instrumentation in accordance with claim 13, wherein the instrumentation comprises an insertion tool which is releasably connectable to the stabilization element, and wherein the marking device or the sensor unit is adapted to be coupled to the insertion tool, at least one of the position and the orientation of the stabilization element being determinable from at least one of the position and the orientation of the marking device relative to the sensor unit.

16. Instrumentation in accordance with claim 13, wherein the instrumentation comprises an indication unit on which indications are displayable for a user for guiding the insertion tool, in order to connect the anchoring elements to one another via the stabilization element.

17. Instrumentation in accordance with claim 1, wherein the instrumentation comprises identification elements allocated to the anchoring elements, a respective identification element being arranged on or included in an anchoring element, and the identification elements differing from one another, and a detection unit for successive, cable-free detection of the identification elements, wherein it is determinable by the data processing unit from signals of the detection unit whether the order in which the identification elements are detected matches a preset or presettable sequence, and a positive or negative indication relating to this being displayable to a user on an indication unit of the instrumentation.

18. Instrumentation in accordance with claim 17, wherein the identification elements are RFID tags or optical identification elements and are detectable by means of RFID technology or optically by the detection unit, this being configured as RFID reader or optical detection unit.

19. Instrumentation in accordance with claim 17, wherein in dependence upon a signal of the detection unit relating to the detection of an identification element, the sensor unit is provided with an activation signal or a reset signal, in order to activate or reset the sensor unit.

20. A method for using medical instrumentation which comprises two or more anchoring elements for anchoring on body tissue and a stabilization element via which the two or more anchoring elements are connectable, wherein a sensor unit is percutaneously selectively coupled to at least one anchoring element or to the stabilization element via a coupling unit, and at least one of the position of the anchoring elements relative to one another and the position of at least one anchoring element relative to the stabilization element is determined by a data processing unit from sensor signals of the sensor unit, the data processing unit generating position data based on the sensor signals of the sensor unit, and the at least one of the position of the anchoring elements relative to one another and the position of at least one anchoring element relative to the stabilization element being defined in a reference coordinate system defined by the sensor unit.

21. Medical instrumentation, comprising two or more anchoring elements for anchoring on body tissue and a stabilization element via which the two or more anchoring elements are connectable, and comprising a sensor unit, a coupling unit for percutaneous selective coupling of the sensor unit to at least one anchoring element or to the stabilization element, and a data processing unit which determines from sensor signals of the sensor unit at least one of the position of the anchoring elements relative to one another, and the position of at least one anchoring element relative to the stabilization element, wherein the instrumentation comprises identification elements allocated to the anchoring elements, a respective identification element being arranged on or included in an anchoring element, and the identification elements differing from one another, and a detection unit for successive, cable-free detection of the identification elements, wherein it is determinable by the data processing unit from signals of the detection unit whether the order in which the identification elements are detected matches a preset or presettable sequence, and a positive or negative indication relating to this being displayable to a user on an indication unit of the instrumentation.

22. Instrumentation in accordance with claim 21, wherein the identification elements are RFID tags or optical identification elements and are detectable by means of RFID technology or optically by the detection unit, this being configured as RFID reader or optical detection unit.

23. Instrumentation in accordance with claim 21, wherein in dependence upon a signal of the detection unit relating to the detection of an identification element, the sensor unit is provided with an activation signal or a reset signal, in order to activate or reset the sensor unit.

* * * * *